United States Patent
Bonnet et al.

(10) Patent No.: US 10,414,704 B2
(45) Date of Patent: *Sep. 17, 2019

(54) PROCESS FOR THE MANUFACTURE OF 2-CHLORO-3,3,3-TRIFLUOROPROPENE BY GAS PHASE FLUORINATION OF PENTACHLOROPROPANE

(71) Applicant: Arkema France, Colombes (FR)

(72) Inventors: Philippe Bonnet, Lyons (FR); Anne Pigamo, Francheville (FR); Laurent Wendlinger, Soucieu en Jarrest (FR); Nicolas Doucet, Lyons (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/014,583

(22) Filed: Feb. 3, 2016

(65) Prior Publication Data

US 2016/0152535 A1 Jun. 2, 2016

Related U.S. Application Data

(63) Continuation of application No. 13/879,036, filed as application No. PCT/IB2010/003030 on Oct. 22, 2010, now Pat. No. 9,284,240.

(51) Int. Cl.
*C07C 17/25* (2006.01)
*C07C 17/20* (2006.01)
*C07C 21/18* (2006.01)
*C07C 17/42* (2006.01)
*B01J 23/86* (2006.01)

(52) U.S. Cl.
CPC .............. *C07C 17/25* (2013.01); *B01J 23/866* (2013.01); *C07C 17/206* (2013.01); *C07C 17/42* (2013.01)

(58) Field of Classification Search
CPC ........ C07C 17/20; C07C 17/206; C07C 17/25
See application file for complete search history.

(56) References Cited

U.S. PATENT DOCUMENTS

| | | | |
|---|---|---|---|
| 4,792,643 A * | 12/1988 | Sobolev | B01J 27/12 570/134 |
| 4,902,838 A | 2/1990 | Manzer et al. | |
| 5,714,651 A | 2/1998 | Elsheikh et al. | |
| 5,811,603 A * | 9/1998 | Elsheikh | C07C 17/00 570/166 |
| 5,900,514 A | 5/1999 | Requieme et al. | |
| 6,184,172 B1 | 2/2001 | Bonnet et al. | |
| 6,235,951 B1 | 5/2001 | Sakyu et al. | |
| 6,455,745 B1 | 9/2002 | Takahashi et al. | |
| 7,485,598 B2 * | 2/2009 | Elsheikh | B01J 23/06 502/224 |
| 9,284,240 B2 * | 3/2016 | Bonnet | C07C 17/206 |
| 2007/0027348 A1 | 2/2007 | Quan et al. | |
| 2009/0030244 A1 | 1/2009 | Merkel et al. | |
| 2009/0240090 A1 | 9/2009 | Merkel et al. | |
| 2011/0224465 A1 * | 9/2011 | Merkel | C07C 17/25 570/156 |

FOREIGN PATENT DOCUMENTS

| | | |
|---|---|---|
| CN | 101687731 A | 3/2010 |
| EP | 0 328 127 A1 | 8/1989 |
| EP | 0 939 071 A1 | 1/1999 |
| GB | 2 030 981 A | 4/1980 |
| JP | H02172933 A * | 7/1990 |
| JP | 9-194404 A | 7/1997 |
| JP | 11-226409 | 8/1999 |
| JP | 2000-34237 A | 2/2000 |
| JP | 2009-227675 A | 10/2009 |
| WO | 2005/108334 A1 | 11/2005 |
| WO | 2007/079431 A2 | 7/2007 |
| WO | 2008/040969 A2 | 4/2008 |
| WO | 2008/054781 A1 | 5/2008 |
| WO | 2009/003084 A1 | 12/2008 |
| WO | 2009/015317 A1 | 1/2009 |
| WO | 2009/118628 A1 | 10/2009 |
| WO | 2009/158321 A1 | 12/2009 |

OTHER PUBLICATIONS

JPH02172933A, Published Jul. 4, 1990; pp. 1-5; English translation (Year: 1990).*

* cited by examiner

*Primary Examiner* — Medhanit W Bahta
(74) *Attorney, Agent, or Firm* — NK Patent Law

(57) ABSTRACT

The present invention provides a process of catalytic fluorination in gas phase of product 1,1,1,2,3-pentachloropropane or/and 1,1,2,2,3-pentachloropropane into product 2-chloro-3,3,3-trifluoropropene in presence of a catalyst and oxygen.

8 Claims, No Drawings

PROCESS FOR THE MANUFACTURE OF 2-CHLORO-3,3,3-TRIFLUOROPROPENE BY GAS PHASE FLUORINATION OF PENTACHLOROPROPANE

CROSS-REFERENCE TO RELATED APPLICATIONS

This application is a Continuation of U.S. patent application Ser. No. 13/879,036 filed Jun. 24, 2013, now allowed; which is a National Stage application of International Application No. PCT/IB2010/03030 filed Oct. 22, 2010.

FIELD OF THE INVENTION

The aim of the invention is the catalytic fluorination in gas phase of product 1,1,1,2,3-pentachloropropane (HCC 240db) and/or 1,1,2,2,3-pentachloropropane (HCC 240aa) into product 2-chloro-3,3,3-trifluoropropene (HCFO 1233xf).

TECHNICAL BACKGROUND

The protocol of Montreal for the protection of the ozone layer led to the end of the use of chlorofluorocarbons (CFCs). Less aggressive compounds for the ozone layer, such as the hydrofluorocarbons (HFCs) e.g. HFC-134a replaced chlorofluorocarbons. These latter compounds were indeed shown to provide greenhouse gases. There exists a need for the development of technologies, which present a low ODP (ozone depletion potential) and a low GWP (global warming potential). Although the hydrofluorocarbons (HFCs), which are compounds which do not affect the ozone layer, were identified as interesting candidates, they exhibit a relatively high GWP value. There still exists the need to find compounds which exhibit a low GWP value. Hydrofluoroolefins (HFO) were identified as being possible alternatives with very low ODP and GWP values.

Several processes for production of HFOs compounds, in particular of propenes, were developed. The two compounds 1233xf (2-chloro-3,3,3-trifluoropropene) and 1234yf (2,3,3,3-tetrafluoropropene) are particularly desired.

US2009/0240090 discloses the gas-phase reaction of 1,1,1,2,3-pentachloropropane (HCC 240db) into product 2-chloro-3,3,3-trifluoropropene (HCFO 1233xf), in the absence of oxygen. Example 3 uses a catalyst comprised of fluorinated $Cr_2O_3$. The product 1233xf thus produced is then converted into product 2-chloro-1,1,1,2-tetrafluoropropane (244bb) in a liquid phase reaction.

WO2009/015317 discloses the reaction of a chlorinated compound, which can be 1,1,2,3-tetrachloro-1-propene (1230xa), 1,1,1,2,3-pentachloropropane (240db) or 2,3,3,3-tetrachloro-1-propene (1230xf) with HF, in gas phase, on a catalyst and in the presence of at least one stabilizer. This process allows obtaining 2-Chloro-3,3,3-trifluoro-1-propene (1233xf). No working example is provided with 240db as a starting material. The stabilizer is said to improve catalyst lifetime. It is also mentioned that periodic regeneration is considered.

WO2005/108334, example 3, discloses that 240db is passed through a flow reactor for a contact time for about 5 to 50 seconds at about 250-400° C. in the presence of 5 molar excess of HF over a 50 g ⅛-inch $Cr_2O_3$ catalyst bed to give 244db (2-chloro-1,1,1,3-tetrafluoropropane). It is further indicated that the 244db is then dehydrochlorinated by passing it over a $Cr_2O_3$ catalyst (50 g) at 425-550° C. with a contact time of 25 to seconds to afford product 1234ze (1,3,3,3-tetrafluoropropene).

GB-A-1091103 discloses a process for manufacturing a chromium fluorination catalyst. Numerous compounds that may be fluorinated using this catalyst are indicated: pentachloropropane is mentioned among others, while not being the preferred compound.

Thus, there is still a need for processes for the production of compound 1233xf.

SUMMARY OF THE INVENTION

The invention provides a process of catalytic fluorination in gas phase of product 1,1,1,2,3-pentachloropropane or/and 1,1,2,2,3-pentachloropropane into product 2-chloro-3,3,3-trifluoropropene in presence of a catalyst and oxygen.

Embodiments are the following:

The ratio of oxygen with respect to pentachloropropane (240) is 0.05 to 15 mole %, preferably 0.5 to 10 mole %.

The process is carried out in the presence of a catalyst comprising Ni—Cr, preferably supported.

The catalyst is supported on a support selected from fluorinated alumina, fluorinated chromia, fluorinated activated carbon or graphite carbon.

The catalyst further comprises a co-catalyst selected from Ni, Co, Zn, Mn or mixtures thereof, preferably nickel, and wherein said co-catalyst is preferably present in an amount from about 1-10 wt % of said fluorination catalyst.

The fluorination catalyst is activated with a fluorine-containing compound, preferably hydrogen fluoride, and preferably at a pressure above 10 bars.

The 1,1,1,2,3-pentachloropropane contains up to 40 mol % of isomer 1,1,2,2,3-pentachloropropane.

The process is carried out at a pressure from 1 to 20 bars, preferably 3 to 15 bars, more preferably 5 to 10 bars.

The process is carried out at a temperature of from 200 to 450° C., preferably from 300 to 430° C., more preferably from 320 to 420° C.

The process is carried out with a contact time from 6 to 100 sec, preferably from 10 to 80 sec, more preferably from 15 to 50 sec.

The process is carried out with a molar ratio HF:240 from 3:1 to 150:1, preferably 4:1 to 70:1, more preferably 5:1 to 50:1.

The process is carried out in the presence of a polymerization inhibitor, preferably chosen from the group consisting of p-methoxyphenol, t-amylphenol, limonene, d,l-limonene, quinones, hydroquinones, epoxides, amines and mixtures thereof.

The process is continuous.

The invention relates to also the products obtained by following the steps of the process disclosed herewith, in particular a mixture containing mainly 1233xf and impurities and/or unreacted starting materials and/or co-products.

DETAILED DESCRIPTION OF EMBODIMENTS

The invention is based on the findings that 240db (and/or 240aa) can be catalytically fluorinated in gas phase into 1233xf, and that process conditions can be selected so as to achieve a reaction with an improved catalyst lifetime, when oxygen is cofed with 240.

Product 240aa will be converted in part into the desired product while the by-products which are presumably of the 243 type can be used usefully in other reactions. Hence, even if starting material 240aa is not completely converted into the desired 1233xf, the products formed otherwise have value.

The catalyst used in the invention is for example a catalyst based on a metal including a transition metal oxide or a derivative or halide or oxyhalide such a metal. Catalysts are e.g. $FeCl_3$, chromium oxyfluoride, chromium oxides (that can optionally be subject to fluorination treatments), chromium fluorides, and mixtures thereof. Other possible catalysts are the catalysts supported on carbon catalysts based on antimony, catalysts based on aluminum (as $AlF_3$ and $Al_2O_3$ and oxyfluoride of alumina and aluminum fluoride). Generally speaking, catalysts that can be used are chromium oxyfluoride, aluminium fluorure and oxyfluoride, and supported or unsupported catalyst containing a metal such as Cr, Ni, Zn, Ti, V, Zr, Mo, Ge, Sn, Pb, Mg. Reference can also be made to the disclosures of WO-A-2007/079431, at page 7, lines 1-5 and 28-32, EP-A-939071, at paragraph [0022], WO2008/054781 at page 9 line 22 to page 10 line 34, WO2008/040969 in claim 1, all incorporated herein by reference.

Prior to its use, the catalyst is subjected to activation, typically with HF at high pressure, typically above about 10 bars (typically at a pressure above the pressure used in the gas-phase process), as described in U.S. Pat. No. 7,485,598, incorporated herein by reference. Any suitable conditions would also be appropriate.

A preferred embodiment uses a particular catalyst, which is a mixed catalyst, containing both chromium and nickel. The molar ratio Cr:Ni, with respect to the metallic element is generally between 0.5 and 5, for example between 0.7 and 2, including close to 1. The catalyst may contain in weight from 0.5 to 20% chromium and 0.5 to 20% nickel, preferably between 2 and 10% of each metal.

The metal may be present in metallic form or as derivatives, including oxide, halide or oxyhalide. These derivatives, including halide and halide oxides, are obtained by activation of the catalytic metal. Although the activation of the metal is not necessary, it is preferred.

The support is preferably made from aluminum. There are several possible carriers such as alumina, activated alumina or aluminum derivatives. These derivatives include aluminum halides and halide oxides of aluminum, for example described in U.S. Pat. No. 4,902,838, or obtained by the activation process described below.

The catalyst may include chromium and nickel in a non-activated or activated form, on a support that has been subjected to activation or not.

Reference can be made to WO2009/118628, and especially to the disclosure of the catalyst from page 4, line 30 to page 7, line 16, which is incorporated herein by reference.

The catalyst can also be a high surface area Cr based catalyst which is preferably unsupported. The catalyst can optionally contain a low level of one or more co-catalyst such as Co, Zn, Mn, Mg and Ni salt. A preferred co-catalyst is nickel. Another preferred co-catalyst is Zn. Another preferred co-catalyst is Mg. A disclosure of the high surface area Cr based catalyst can be found in WO2009/158321, pages 4 and 6). The process of the present invention is preferably run continuously.

The present fluorination process involves contacting 240db with HF in the reaction zone in a gas phase, under conditions sufficient to convert the 240db to fluorination products comprising mainly 1233xf.

Typically, the process of the invention is carried out with a molar ratio HF:240 from 3:1 to 150:1, preferably 4:1 to 70:1, more preferably 5:1 to 50:1.

Typically, the process of the invention is carried out at a pressure from 1 to 20 bars, preferably 3 to 15 bars, more preferably 5 to 10 bars.

Typically, the process of the invention is carried out at a temperature of from 200 to 450° C., preferably from 300 to 430° C., more preferably from 320 to 420° C. The temperature of the bed can be substantially uniform in the reactor or can be adjusted along the path of the stream, decreasing or increasing along the direction of flow.

Contact times (catalyst volume divided by the total flow rate of reactants and co-feeds, adjusted to the operating pressure and temperature) are typically from 6 to 100 sec, preferably from 10 to 80 sec, more preferably from 15 to 50 sec.

An oxygen co-feed is used to extend the catalyst lifetime, typically in an amount of from 0.05 to 15 mole %, preferably 0.5 to 10 mole % of oxygen or chlorine per pentachloropropane molecule. The oxygen can be introduced as an oxygen-containing gas such as air, pure oxygen, or an oxygen/nitrogen mixture.

A polymerization inhibitor can be used to extend the catalyst life, typically in a concentration of from about 50-1000 ppm, more preferably between 100-500 ppm. The polymerization inhibitor can be p-methoxyphenol, t-amylphenol, limonene, d,l-limonene, quinones, hydroquinones, epoxides, amines and mixtures thereof. The preferred polymerization inhibitor is p-methoxyphenol or t-amylphenol. The co-feeding of a low level of a polymerization inhibitor can control such polymerization of chloroolefins and extend the life of the catalyst as described in U.S. Pat. No. 5,714,651, incorporated herein by reference.

The reactants can be fed to the reactor at the same location, at different locations, or using staged feeding at staged locations along the reactor. A preferred feeding system is to blow the gaseous reactants at the bottom of the reactor. Recycling can be done at the entry of the reactor or at an intermediate stage of the reactor; preferably at the entry of the reactor. It is also possible to recycle part of the stream exiting the reactor.

Reactions are implemented in a dedicated reactor for reactions involving halogens. Such reactors are known to those skilled in the art and can include linings based eg Hastelloy®, Inconel®, Monel® or fluoropolymers. The reactor may also include means of heat exchange, if necessary.

The final product is readily recovered by any means known in the art, such as by scrubbing, washing, extraction, decantation and preferably distillation. It can also be further purified by distillation techniques.

EXAMPLES

The following examples illustrate the invention without limiting it.

The equipment used consists of a tubular reactor of an internal diameter of 19 mm, made of INCONEL® alloy 600 surrounded by a tubular oven. It is also equipped with pressure and temperature controller. The reactants, preliminarily vaporized thanks a heater, are introduced in gaseous phase at the top of the reactor.

At the outlet of the reactor, a sample of the products of the reaction is taken, washed by a pre-column and analyzed online by a gas phase chromatography equipped with low polarity capillary column.

The analysis by chromatography is carried out using a column CP Sil 8CB, dimensions 50 m*0.32 mm*5 μm. The programming of temperature of the oven is the following one: 70° C. during 10 min then slope of 10° C./min until 250° C.

Considering that xi is the initial amount of moles of raw material and xf the total final amount of moles of raw material, conversion (%) is: (xi−xf)/xi*100. Selectivity of a product is calculated by the ratio between the amount of moles recovered of this product and the total amount of moles of products of reaction.

The molar ratio of HF (MR HF) is defined as the ratio between the molar flow rate of HF and the molar flow rate of 1,1,1,2,3-pentachloropropane.

Example 1

Fluorination of 240db (1,1,1,2,3-pentachloropropane) is performed in the reactor described above with 79.4 cm³ of Ni—Cr catalyst supported on AlF$_3$.

The catalyst used is a mixed catalyst nickel/chromium of atomic ratio of Ni/Cr=1, supported on alumina fluoride and is prepared by impregnating solutions of nickel and chromic anhydride (CrO$_3$). After impregnation and drying, the solid is treated at a temperature between 320° C. and 390° C. in the presence of a mixture of hydrofluoric acid and nitrogen (concentration by volume of 5 to 10% of this acid in nitrogen).

The reactor was continuously fed with 15 g/hr of anhydrous HF and about 4.5 g/hr of 1,1,1,2,3-pentachloropropane at atmospheric pressure for 86 hrs. Thus, the contact time is 7.4 seconds, the molar ratio of HF to 240 is 36, and the reaction temperature is 340° C. The amount of oxygen is about 4 mol % with respect to the 240db. Results are given in the table 1.

Example 2

Fluorination of the mixture of 65.9 mol % of 240db or 1,1,1,2,3-pentachloropropane and 34.9 mol % of 240aa or 1,1,2,2,3-pentachloropropane is performed according to example 1 described above. The reactor was continuously fed with 16 g/hr of anhydrous HF and about 5.1 g/hr of 1,1,1,2,3-pentachloropropane at atmospheric pressure. Thus, the contact time is 6.9 seconds, the molar ratio is 34, and the reaction temperature is from 340° C. The amount of oxygen is about 4 mol % with respect to the total number of mole of 1,1,1,2,3-pentachloropropane and 1,1,2,2,3-pentachloropropane. Results are given in table 1.

Examples 3 and 4

Example 2 is repeated at different temperatures as indicated in table 1.

TABLE 1

| | Temp. ° C. | Conversion % | Selectivity (Area (%)) | | |
| | | | 1234yf + 245cb | 1233xf | others |
| --- | --- | --- | --- | --- | --- |
| Ex. 1 | 340 | 100% | 1.6 | 98.3 | 0 |
| Ex. 2 | 340 | 100% | 0.5 | 72.0 | 25.6 |
| Ex. 3 | 360 | 100% | 0.5 | 72.0 | 25.1 |
| Ex. 4 | 380 | 100% | 0.6 | 74.3 | 22.8 |

No deactivation is seen in example 1 after 86 hours. Further, it is remarkable that the selectivity remains very high.

The invention claimed is:

1. A catalytic fluorination process for producing 2-chloro-3,3,3-trifluoropropene comprising:
    activating a fluorination catalyst with a fluorine-containing compound, wherein the fluorination catalyst is a chromium catalyst further comprising a zinc co-catalyst, said zinc co-catalyst being present in an amount from about 1-10 wt % of said fluorination catalyst, and
    reacting 1,1,1,2,3-pentachloropropane and/or 1,1,2,2,3-pentachloropropane in a gas phase in the presence of HF, oxygen, and the activated fluorination catalyst and the absence of a polymerization stabilizer, wherein the fluorination reaction takes place at a reaction pressure and activating the fluorination catalyst takes place at a pressure above the reaction pressure.

2. The process according to claim 1, wherein the ratio of oxygen with respect to 1,1,1,2,3-pentachloropropane and/or 1,1,2,2,3-pentachloropropane is 0.05 to 15 mole %.

3. The process according to claim 1, wherein said catalyst is supported on a support selected from the group consisting of fluorinated alumina, fluorinated chromia, fluorinated activated carbon and graphite carbon.

4. The process according to claim 1, wherein the 1,1,1,2,3-pentachloropropane contains up to 40 mol % of isomer 1,1,2,2,3-pentachloropropane.

5. The process according to claim 1, wherein the process is carried out at a temperature of from 200 to 450° C.

6. The process according to claim 1, wherein the process is carried out with a contact time from 6 to 100 sec.

7. The process according to claim 1, wherein the process is carried out with a molar ratio HF:240 from 3:1 to 150:1.

8. The process according to claim 1 wherein the process is continuous.

* * * * *